United States Patent [19]
Öhlschlager et al.

[11] 3,984,246
[45] Oct. 5, 1976

[54] ANTIHALATION AND FILTER DYES FOR PHOTOGRAPHIC MATERIALS

[75] Inventors: Hans Öhlschläger, Schildgen; Oskar Riester; Franz Moll, both of Leverkusen, all of Germany

[73] Assignee: AGFA-Gevaert, A.G., Leverkusen, Germany

[22] Filed: Nov. 4, 1975

[21] Appl. No.: 628,755

[30] Foreign Application Priority Data

Nov. 9, 1974 Germany ............................ 2453217

[52] U.S. Cl. ............................ 96/84 R; 260/310 A; 260/240.2

[51] Int. Cl.[2] ..................... G03C 1/84; C09B 23/00; C07D 231/00

[58] Field of Search ....................... 96/84 R, 84 UV; 260/310 A, 240.2

[56] References Cited

UNITED STATES PATENTS

| | | | |
|---|---|---|---|
| 2,274,782 | 3/1942 | Gaspar | 96/69 |
| 3,647,460 | 3/1972 | Hofman et al. | 96/84 R |
| 3,726,682 | 4/1973 | Paesschen et al. | 96/84 R |
| 3,795,519 | 3/1974 | Miyazako et al. | 96/84 R |
| 3,865,817 | 2/1975 | Kobayaski et al. | 96/84 R |
| 3,932,188 | 1/1976 | Tanaka et al. | 96/84 R |

*Primary Examiner*—Jack P. Brammer
*Attorney, Agent, or Firm*—Connolly and Hutz

[57] ABSTRACT

Photographic materials containing in at least one photographic layer as antihalation- or filter-dyes mono-, tri- or pentamethineoxonoles of 1-sulfolanyl pyrazolones, which dyes can be easily decolorized and washed out on treatment of the photographic material in photographic processing.

5 Claims, No Drawings

ANTIHALATION AND FILTER DYES FOR PHOTOGRAPHIC MATERIALS

This invention relates to photographic materials which contain in at least one photographic layer as an antihalation or filter dye at least one mono-, tri- or pentamethine oxonol of 1-sulpholanyl pyrazolones.

It is customary to coat the back of roll films and sheet films with coloured gelatine layers. These layers are intended to prevent the film from curling up (NC-layers) and to absorb as completely as possible the light not absorbed by the emulsion layers, in order to prevent the formation of reflected light halation. A further improvement can be achieved by arranging the antihalation layer as a filter layer immediately under the emulsion layer instead of on the back of the film.

Dyes which are intended for such NC and filter layers must fulfil numerous cnditions. For example, they must have good absorption properties and they must be capable of being bleached completely and irreversibly in conventional photographic baths. They should also be readily soluble or dispersible so that they can be introduced at sufficient concentrations into the layers but at the same time they must be fixed in the layer so that if the film material is rolled up they will not migrate from the NC-layers into adjacent emulsion layers or diffuse from a filter layer into an adjacent emulsion layer.

Filter layers are particularly important in multilayered colour photographic materials. For example, it is known that a filter layer containing a dye which absorbs green light may be arranged between a green-sensitive layer and a red-sensitive layer underneath it in order to improve the sharpness and the reproduction of green in the region of strong exposure. Such a dye must not only satisfy the usual requirements of black and white materials, such as resistance to diffusion and to discolouration, but it must also have special absorption properties. For example, in the case described above the dye must have a very steep drop to the regions of longer wavelengths so that the red light can enter undiminished into the layer underneath it.

The most important dyes for use as antihalation and filter dyes are those of the oxonol type, the dyes used as antihalation layers being generally oxonol dyes of the pyrazolone series.

It is known that numerous pentamethine oxonol dyes can be irreversible decolourised in the usual photographic baths but trimethine oxonols and monomethine oxonols will only undergo slight decolourisation. In practice, therefore, only those dyes have hitherto been used which can easily be washed out of the photographic material by virtue of the presence of groups which render them soluble, such as sulpho or carboxyl groups. Reference may be made in this connection to the dyes described in U.S. Pat. No. 2,274,782 or in German Offenlegungsschriften Nos. 2,259,746, 2,231,470 and 2,026,252.

Among the known filter dyes, those which can easily be washed out as a result of their solubilising groups are generally not sufficiently resistant to diffusion in the photographic layers. Dyes which have been fixed in a diffusion-resistant form by the introduction of longer fatty radicals into the dye molecule are generally difficult to wash out in spite of the presence of water-solubilising groups.

For the rapid processing of photographic materials, in which the various stages of the process should be completed within a very short time, the filter dyes must satisfy even higher standards with regard to the possibility of decolourising and washing them out. Processing colour-photographic paper is particularly critical because this must generally be carried out with very short development times and any residual colour density in the filter dyes or antihalation dyes is particularly noticeable.

It is therefore necessary in practice to find improved dyes which are suitable for use as antihalation and filter dyes without having the disadvantages of the dyes known in the art. The antihalation dyes may also be regarded as sharpening and correcting dyes.

The dye should therefore fulfil the following conditions:

a. It must have a suitable spectral absorption for the purposes of the layer in which it is used.
b. It must be photographically inert. For example, it must not desensitise a photographic silver halide emulsion or cause fogging if it is incorporated in a photographic material.
c. The dye must be rapidly and completely bleached and removed when the light-sensitive material is processed. A dye which dissolves in the treatment solution, for example the developer solution, when it is in the coloured state is unsuitable because it would contaminate the treatment solution and the photographic materials treated in this solution.

It has now been found that the problem described above can be solved very satisfactorily if a light-sensitive photographic material which has at least one photographic layer coloured by a dye contains at least one monomethine, trimethine or pentamethine oxonol of 1-sulpholanyl-pyrazolon, or a water-soluble salt thereof.

The dyes according to the invention are preferably characterised by the following general formula:

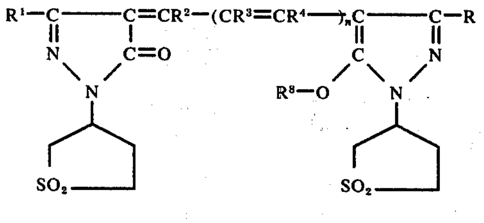

wherein

R and $R^1$ may be identical or different and denote 1. an alkyl group which may be substituted or unsubstituted, for example a methyl group, an ethyl group, a hydroxyethyl group, a cyanoethyl group, a hydroxyethoxyethyl group, a propyl group, an isopropyl group, a butyl group, a tertiary butyl group, a hexyl group, an octyl group, a decyl group, a dodecyl group, a pentadecyl group, an octadecyl group, a benzyl group and the like,
2. an aryl group which may be substituted or unsubstituted, for example a phenyl group, a tolyl group, an ethyl group, a chlorophenyl group, a methoxyphenyl group, a naphthyl group and the like,
3. a carboxylic acid group or carboxylic acid ester group: $COOR^5$, or
4. a carboxylic acid amide group: $CO—NR^6R^7$;

$R^2$, $R^3$ and $R^4$ represent hydrogen or a lower alkyl group preferably containing up to 4 C-atoms, such as methyl or ethyl, or an aryl group, such as phenyl;

$R^5$, $R^6$ and $R^7$ represent 1. hydrogen,
2. an alkyl group which may be substituted or unsubstituted, for example a methyl group, an ethyl group, a hydroxyethyl group, a cyanoethyl group, a hydroxyethoxyethyl group, a propyl group, an isopropyl group, a butyl group, a tertiary butyl group, a hexyl group, an octyl group, a decyl group a dodecyl group, a pentadecyl group, an octadecyl group, a benzyl group and the like,
3. an aryl group which may be substituted or unsubstituted, for example a phenyl group, a tolyl group, an ethylphenyl group, a chlorophenyl group, a methoxyphenyl group, a naphthal group and the like;

$R^6$ and $R^7$ may also together represent, together with the adjoining N-atom, the ring members required for completing a heterocyclic ring, for example for completing one of the following rings: pyrrolidine, piperidine, cyclohexamethylene imine, indoline, tetrahydroquinoline, morpholine, thiomorpholine, piperazine or N-methyl piperazine;

$R^8$ denotes hydrogen, or any cation which forms watersoluble salts, such as inorganic or organic ammonium salts such as $NH_4^+$, pyridinium or alkali metal salts such as lithium, sodium or potassium; and $n = 0,1$ or 2.

The properties of the dyes, such as their solubility, resistance to diffusion and ability to be decolourised, can be adjusted as desired by a suitable choice of the substituents $R^1$ and $R^2$ and can thereby be adapted for their individual purpose. The compounds of the above formula may, of course, also be used in the form of their salts, for example their salts with alkali metal or amines of any kind.

Examples of suitable compounds are summarised in the following Table:

Table 1

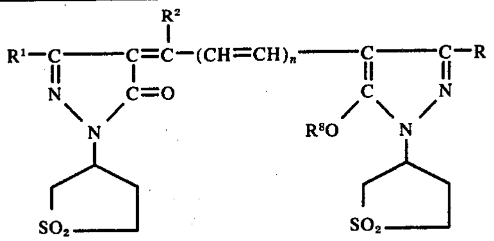

| Dye No. | $R^1$ | R | $R^2$ | n | $R^8$ | Absolute Max. (nm) | Solvent |
|---|---|---|---|---|---|---|---|
| 1 | 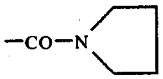 | 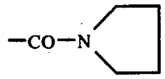 | H | 0 | H | 416 | Acetonitrile |
| 2 | " | " | H | 1 | K | 542 | Methanol |
| 3 | " | " | H | 2 | K | 638 | Methanol |
| 4 | $COOC_2H_5$ | $COOC_2H_5$ | H | 0 | H | 432 | Methanol |
| 5 | " | " | H | 1 | Na | 556 | Methanol |
| 6 | " | " | H | 2 | K | 649 | Methanol |
| 7 | COOH | COOH | H | 0 | H | 426 | Acetonitrile |
| 8 | COOH | COOH | H | 1 | H | 533 | Water |
| 9 | COOK | COOK | H | 2 | K | 625 | Water |
| 10 | $CH_3$ | $CH_3$ | H | 1 | H | 518 | Methanol |
| 11 | $CH_3$ | $CH_3$ | H | 2 | K | 618 | Methanol |
| 12 | 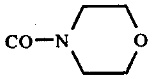 | 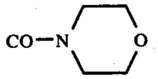 | H | 0 | K | 419 | Acetonitrile |
| 13 | " | " | H | 1 | K | 543 | Methanol |
| 14 | $CO-NH_2$ | $CO-NH_2$ | H | 1 | K | 542 | Water |
| 15 | " | " | H | 2 | K | 643 | Methanol |
| 16 | $CO-NH-C_6H_{13}$ | $CO-NH-C_6H_{13}$ | H | 1 | K | 548 | Methanol |
| 17 | " | " | H | 2 | K | 644 | Methanol |
| 18 | $CO-NH-C_2H_5$ | $CO-NH-C_2H_5$ | H | 1 | K | 548 | Methanol |
| 19 | " | " | H | 2 | K | 643 | Methanol |
| 20 | $CO-NH-C_6H_5$ | $CO-NH-C_6H_5$ | H | 1 | K | 554 | Methanol |
| 21 | " | " | H | 2 | K | 648 | Methanol |
| 22 | $CH_3$ | $CH_3$ | $CH_3$ | 1 | Na | 533 | Methanol |
| 23 | $CO_2C_2H_5$ | $CH_3$ | H | 1 | K | 536 | Methanol |

Column 8, in the above Table shows the solvent in which measurement of the UV spectrum was carried out in the usual manner.

The dyes which are to be used according to the invention may be prepared by the usual methods. For example, mono-, tri- or pentamethine oxonols of 1-sulpholanyl-pyrazolones can be obtained by reacting the corresponding pyrazolones with the necessary methine chain formers in a suitable solvent in the presence of a basic condensing agent such as pyridine or triethylamine. The synthesis of 1-sulphonylanyl-pyrazolone is carried out by condensation of a ketocarboxylic acid ester with sulpholanyl hydrazine in the usual manner. The preparation of sulpholanyl hydrazine has been described in Annalen der Chemie, Volume 681, pages 105–110 (1965. Asymmetric dyes may be prepared, for example, by the methods described in U.S. Pat. No. 2,611,696. The preparation of some of the dyes is described in detail below.

Dye No. 1

2.3 g of 1-sulpholanyl-pyrazolone-3-carboxylic acid pyrrolidide and 5 ml of triethyl orthoformate in 15 ml of pyridine are heated under reflux for 15 minutes. The dye precipitates on cooling and is suction-filtered and purified by reprecipitation from pyridine/isopropanol.

Yield: 1.4 g, mp. 278°C.

Dye No. 5

5.4 g of 1-sulpholanyl-pyrazolone-3-carboxylic acid ethyl ester and 1.8 g of tetramethoxypropane in 5 ml of pyridine are heated on a steam bath for 45 minutes. The solution is cooled and the dye is precipitated with 25% aqueous sodium chloride solution, suction-filtered and recrystallised from methanol.

Yield: 2.5 g, mp. 202°C.

Dye No. 9

4.9 g of 1-sulpholanyl-pyrazolone-3-carboxylic acid and 2.8 g of glutaconaldehyde-dianilide hydrochloride in 15 ml of pyridine and 3 ml of triethylamine are stirred at room temperature for 20 minutes. The dye is isolated from its solution by precipitation with ether and decanting of the supernatant solution. It is then triturated with methanolic potassium acetate solution, suction-filtered and purified with methanol.

Yield: 3.1 g, mp. 290°C.

The other dyes given in the above Table are prepared in an analogous manner.

The dyes according to the invention may be used for any conventional photographic materials which contain one or more light-sensitive silver halide emulsion layers. They may also be mixed with other dyes.

The dyes according to the invention may be used as antihalation dyes in back-coating layers, as filter or correction dyes in special intermediate or top-coating layers, or as screening dyes in emulsion layers.

When used as antihalation layers, the layers containing the dyes according to the invention may be applied to one or both sides of the support. They may be arranged either on the back of the support or between the support and the lightsensitive layer.

The materials according to the invention may be, for example, positive, negative or reversal materials containing the usual layer supports used in known manner for the preparation of photographic materials. Suitable layer supports include, for example, foils of cellulose nitrate, cellulose acetate such as cellulose triacetate, polystyrene, polyesters such as polyethylene terephthalate, polyolefines such as polyethylene or polypropylene, a baryta paper support, a polyolefine laminated paper support, e.g. a polyethylene laminated paper support, or glass.

The binder used for the antihalation layers or filter layers is preferably gelatine but it may be partly or completely replaced by other hydrophilic binders such as polyvinyl alcohols, poly-N-vinyl pyrolidone, carboxymethyl cellulose or in fact any cellulose derivatives, alginic acid or its derivatives, etc. Before they are incorporated in the photographic material, the dyes according to the invention are first dissolved in the usual manner in water or a mixture of water and a water-soluble solvent such as a lower alcohol and added to the gelatine casting solution. The layers which contain the dyes are cast and dried in the usual manner. The finished layers contain the dyes in quantities of from 100 to 1000 mg/m$^2$, depending on the purpose of which they are to be used and the desired colour density.

If the dyes according to the invention are to be used in light-sensitive emulsions, it is suitable to use emulsions of silver halides such as silver chloride, silver bromide or mixtures of the two, if desired with a small silver iodide content of up to 10 mol-%, in one of the usual hydrophilic binders.

The light-sensitive emulsions may be chemically sensitised by carrying out the ripening of the emulsions in the presence of small quantities of sulphur compounds such as allyl isothiocyanate, allyl thiourea, or sodium thiosulphate. The light-sensitive emulsions may also be sensitised with the tin compounds described in Belgian Patent Specification Nos. 493,464 and 568,687, with polyamines such as diethylene triamine or the iminoaminoethane sulphinic acid compounds described in Belgian Patent Specification No. 547,323, or with small quantities of compounds of noble metals such as gold, platinum, palladium, iridium, ruthenium or rhodium. This method of chemical sensitisation has been described in the article by R. KOSLOWSKY, Z Wiss. Phot. 46, 65–72 (1951). The emulsions may also be sensitised with polyalkylene oxide derivatives such as a polyethylene oxide with a molecular weight of between 100 and 20 000 or with condensation products of alkylene oxides and aliphatic alcohols, glycols, cyclic dehydration products of hexitols, alkyl-substituted phenols, aliphatic carboxylic acids, aliphatic amines, aliphatic diamines and amides.

The condensation products should have a molecular weight of at least 700 and preferably more than 1000. These sensitisers may, of course, also be combined to produce special effects, as described in Belgian Patent Specification No. 537,278 and in British Patent Specification No. 727,982.

If the dyes according to the invention are to be used in emulsions which contain colour couplers, these emulsions may also contain spectral sensitisers, e.g. the usual monomethine or polymethine dyes such as cyanines hemicyanines, streptocyanines, merocyanines, oxonols, hemioxonols, styryl dyes or others, including also trinuclear or higher nuclear methine dyes, for example rhodacyanines or neocyanines. Sensitisers of this kind have been described, for example, in the work by F. M. Hamer "The Cyanine Dyes and Related Compounds" (1964) Interscience Publishers John Wiley and Sons, New York.

The emulsions may contain conventional stabilisers, e.g. homopolar or salt compounds of mercury which contain aromatic or heterocyclic rings such as mercaptotriazoles, simple mercury salts, sulphonium mercury double salts and other mercury compounds. Azaindenes are also suitable stabilisers, particularly tetra- or pentaazaindenes and especially those which are substituted with hydroxyl or amino groups. Compounds of this kind have been described in the article by BIRR, Z. Wiss. Phot. 47, 2 – 27 (1958). Other suitable stabilizers include heterocyclic mercapto compounds, e.g. phenyl mercaptotetrazole, quaternary benzothiazole derivatives, benzotriazole and the like.

The emulsions may be hardened by conventional methods, for example with formaldehyde or halogenated aldehydes which contain a carboxyl group, such as mucobromid acid, diketones, methane sulphonic acid esters, dialdehydes and the like.

The photographic layers may also be hardened with epoxide hardeners, heterocyclic ethylene imine hardeners or acryloyl hardeners. Examples of such hardeners have been described, for example, in German Offenlegungsschrift No. 2,263,602 and in British Patent Specification No. 1,266,655. The layers may also be hardened by the process according to German Offenlegungsschrift No. 2,218,009 in order to obtain colour photographic materials which are suitable for high temperature processing.

The photographic layers or colour photographic multilayered materials may also be hardened with hardeners of the diazine, triazine or 1,2-dihydroquinoline series as described in British Patent Specifications Nos. 1,193,290, 1,251,091, 1,306,544 and 1,266,655, in French Patent Specification No. 7,102,716 or in German Offenlegungsschrift 2,332,317. Examles of such hardeners include diazine derivatives which contain alkyl or aryl sulphonyl groups, derivatives of hydrogenated diazines or triazines, e.g. 1,3,5-hexahydrotriazine, fluorinated diazine derivatives, e.g. fluoropyrimidines, esters of 2-substituted 1,2-dihydroquinoline- or 1,2-dihydroisoquinoline-N-carboxylic acids. Vinyl sulphonic acid hardeners, carbodiimide hardeners and carbamoyl hardeners such as those described, for example, in German Offenlegungsschriften No. 2,263,602, 2,225,230 and 1,808,685, in French Patent Specification No. 1,491,807, in German Patent Specification No. 872,153 and in DDR Patent Specification No. 7,218 may also be used. Other suitable hardeners have been described, for example, in British Patent Specification No. 1,268,550.

Suitable wetting agents which may be used in the process of the invention to incorporate the dyes according to the invention have been described by Gerhard GEWALEK in "Wasch- und Netzmittel", Akademie-Verlag Berlin (1962). The following are examples: the sodium salt of N-methyl-oleyl tauride, sodium stearate, the sodium salt of heptadecenyl benzimidazole sulphonic acid, sodium sulphonates of higher aliphatic alcohols, e.g. 2-methyl-hexanol sodium sulphonate, sodium diiso-octyl sulphosuccinate, sodium dodecyl sulphonate and the sodium salt of tetradecyl benzene sulphonic acid.

The photographic layers may also contain the usual colour couplers. Suitable colour couplers include in general the usual colourless compounds which react with oxidation products of colour developer substances to form azomethine or azo dyes. For example, the cyan couplers used are generally compounds derived from phenol or α-naphthol, e.g. naphthanilides or 2-aminophenol derivatives; the purple couplers are generally compounds derived from 2-pyrazolinone-5 or indazolone, e.g. 3-acylamino or 3-anilinopyrazolinone-5 compounds, particularly those substituted by a phenyl group in the 1-position; the yellow couplers are generally derived from β-ketocarboxylic acid derivatives, e.g. from benzoyl acetanilides or pivaloyl acetanilides. Couplers which are not substituted in the coupling position, so-called 4-equivalent couplers or couplers which carry in the coupling position a substituent which is split off in the reaction with the developer oxidation products, so-called 2-equivalent couplers, or DIR-couplers which release a development inhibitor may be used. Examples of conventional colour couplers have been described e.g. in the article by W. PELZ in "Mitteilungen aus den Forschungslaboratorien der Agfa Leverkusen-Munchen" Volume 3, page 111.

Conventional colour developers are used for producing the dyes, for example the usual aromatic compounds of the p-phenylene diamine series which contain at least one primary amino group.

Suitable colour developers include, for example, N,N-dimethyl-p-phenylene diamine, N,N-diethyl-p-phenylene diamine, monomethyl-p-phenylene diamine, 2-amino-5-diethylamino-toluene, N-butyl-N-ω-sulphobutyl-p-phenylene diamine, 2-amino-5-(N-ethyl-N-β-methane sulphonamidoethylamino)-toluene and the like. Other suitable colour developers have been described, for example, in J. Amer. Chem. Soc. 73, 3000 – 3025 (1951).

The dyes according to the invention may advantageously be fixed in the layer with basic mordants. By basic mordants are meant the known amines, quaternary ammonium compounds and guanidines which carry long fatty acid groups or are attached to polymer groups, e.g. the compounds described in U.S. Pat. Nos. 3,016,306, 3,740,228 and 2,882,156.

The dyes which are to be used according to the invention are distinguished by the exceptional ease and rapidity with which they can be decolourised in the usual photographic treatment processes. Their decolourisation is even better than that of similar pyrazolone oxonols which have a molecular size comparable with that of the dyes according to the invention. In addition, the adherence of the dyes according to the invention to the usual hydrophilic binders used in photographic materials is surprisingly found to be considerably less, although the dyes according to the invention do not contain any solubilising groups in the usual sense. The dyes according to the invention are therefore eminently suitable both for conventional photographic materials as well as for materials used for high-speed processing. Their use in colour photographic papers is exceptional advantageous and they produce no colour fog even in colour photographic papers with very short development times. In contrast known compounds usually produce such a fog owing to residual dye left in the photographic material.

In the following Examples all percentages are by weight unless otherwise specified.

EXAMPLE 1

$2.5 \cdot 10^{-4}$ mol of a trimethine oxonol and $2.0 \cdot 10^{-4}$ mol of a pentamethine oxonol were each dissolved in 50 ml of water and added to 130 ml of a 10% gelatine solution. 5 ml of a 10 % saponin solution were then added as a wetting agent in each case the resulting dye solution was directly cast onto a cellulose support after the addition of a hardener, e.g. 0.3 ml of a 30% aqueous formaldehyde solution, and then dried. To determine the residual colour density, the samples were put under running water and the residual density was determined after 3, 5 and 8 minutes. The results obtained are summarised in Table 2 below. Compounds I to IV are comparison dyes known in the art which contain solubilising groups.

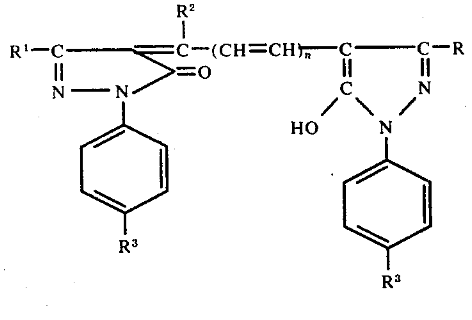

Comparison dye I : $R^1$ and $R = CO_2C_2H_5$, $R^2 = H$, $R^3 = COOH$, $n = 1$

Comparison dye II : $R^1$ and $R = CH_3$, $R^2 = CH_3$, $R^3 = SO_3Na$, $n = 1$

Comparison dye III : $R^1$ and $R = CH_3$, $R^2 = H$, $R^3 = SO_3H$, $n = 1$

Comparison dye IV : $R^1$ and $R = CO_2C_2H_5$, $R^2 = H$, $R^3 = SO_3K$, $n = 2$

TABLE 2

| Dye No. | Quantity $10^{-4}$ Mol | λMax. in gelatine | Density at λmax. and after washing untreated | 3 min. | 5 min. | 8 min. | Residual colour (%) after washing 3 min. | 5 min. | 8 min. |
|---|---|---|---|---|---|---|---|---|---|
| Comparison | | | | | | | | | |
| Dye I | 2.5 | 555[(1)] | 1.25 | 0.51 | 0.36 | 0.18 | 41 | 29 | 14 |
| " II | 2.5 | 545 | 1.04 | 0.63 | 0.43 | 0.19 | 61 | 41 | 18 |
| " III | 2.5 | 532 | 1.15 | 0.71 | 0.50 | 0.22 | 62 | 43 | 19 |
| " IV | 2.0 | 665 | 1.34 | 0.78 | 0.40 | 0.15 | 58 | 29 | 11 |
| 2 | 2.5 | 552 | 1.31 | 0.01 | — | — | 0.8 | — | — |
| 3 | 2.0 | 652 | 1.22 | 0.04 | 0.02 | — | 3.3 | 2 | — |
| 5 | 2.5 | 563 (528)[(2)] | 1.10 | 0.47 | 0.22 | 0.02 | 42 | 20 | 1.8 |
| 6 | 2.0 | 655 (620)[(2)] | 0.97 | 0.36 | 0.17 | 0.02 | 37 | 18 | 2 |
| 9 | 2.0 | 651 | 1.19 | — | — | — | — | — | — |
| 10 | 2.5 | 525 | 1.26 | 0.01 | — | — | 0.8 | — | — |
| 14 | 2.5 | 559 | 1.35 | 0.05 | 0.01 | — | 3.7 | 0.7 | — |
| 15 | 2.0 | 658 | 1.44 | 0.10 | 0.03 | — | 7 | 2 | — |
| 19 | 2.0 | 657 | 1.40 | 0.06 | 0.03 | — | 4.3 | 2 | — |
| 22 | 2.5 | 538 | 1.24 | 0.03 | 0.01 | — | 2.4 | 0.8 | — |

[(1)]Colour change under rinsing
[(2)]Dyes produce a pronouced side maximum in gelatine The comparison experiments clearly show that, even if the dyes according to the invention contain no additional water-solubilising groups they can be washed out more completely than comparison dyes which contain sulpho or carboxyl groups. The dyes according to the invention shown in Table 2 can be used directly in the gelatine solution described above for producing an antihalation layer or they may be added to a silver halide emulsion layer as screening or sharpening dyes.

EXAMPLE 2

2.5 · $10^{-4}$ mol of a dye in aqueous solution were added in each case to 1 kg of a silver chloride emulsion which had been sensitised with a sensitiser for the green spectral region. The emulsions were cast onto a paper support and the photographic materials obtained in this way were dried and developed in a developer of the following composition for 2 minutes:

| | |
|---|---|
| p-aminophenol | 1 g |
| hydroquinone | 3 g |
| sodium sulphite sicc. | 13 g |
| soda sicc. | 26 g |
| potassium bromide | 1 g |
| made up to 1 l with water. | |

The dyes added to the individual emulsions are shown in Table 3 below. After development, the photographic materials were fixed in the usual manner and dried and the colour of the individual materials was assessed visually. The formulae of the comparison dyes I to III are given in Example 1 above.

Table 3

| Dye No. | Residual colour |
|---|---|
| none | none |
| Comparison dye I | orange red |
| Comparison dye II | deep pink |
| Comparison dye III | deep pink |
| 2 | none |
| 5 | none |
| 8 | none |
| 10 | very pale pink |
| 13 | none |

Table 3-continued

| Dye No. | Residual colour |
|---|---|
| 14 | very pale pink |
| 18 | none |
| 22 | very pale pink |

As the results show, the dye layers according to the invention are decolourised much more completely than the comparison dyes.

EXAMPLE 3

The experiments described in Example 2 were repeated except that, instead of using a silver chloride emulsion, a silver iodo bromide emulsion containing a purple coupler 1-(4'-phenoxy-3'-sulphophenyl)-3-heptadecyl-pyrazolone-5 was used. After exposure, the samples were developed in a conventional colour developer of the composition indicated below which contained a paraphenylene diamine colour developer as developer substance, and they were then bleach-fixed. The colour was then assessed as indicated in Example 2. The dyes used in the various samples are indicated in Table 4 below.

Table 4

| Dye No. | Residual colour |
|---|---|
| none | none |
| Comparison dye I | orange red |
| Comparison dye II | deep pink |
| Comparison dye III | deep pink |
| 2 | none |
| 5 | very pale orange red |
| 8 | none |
| 10 | none |
| 13 | nonc |
| ·14 | none |
| 18 | none |
| 22 | none |

The developer has the following composition:

| | |
|---|---|
| Hydroxylamine sulphate | 3 g |
| N-butyl-n-ω-sulphobutyl-p-phenylene diamine | 6 g |
| Potassium carbonate sicc. | 87 g |
| Potassium bromide | 1 g |
| Sodium sulphite sicc. | 5 g |
| Sodium hexametaphosphate | 2 g |
| Water up to 1 l. | |

EXAMPLE 4

50 mg of dye No. 19 in methanolic solution were added to 100 ml of a red-sensitised silver iodobromide emulsion containing the sodium salt of 1-hydroxy-4-sulpho-N-octadecyl-2-naphthamide as a cyan coupler. The blue coloured emulsion solution was then applied to a polyester support which had been covered with a bonding layer.

The photographic material was then divided into several samples and each sample was developed in a developer of the following composition and bleached and fixed in the usual manner:

| | | |
|---|---|---|
| Diethyl-p-phenylene diamine sulphate | 2.75 | g |
| Hydroxylamine sulphate | 1.2 | g |
| Sodium sulphite sicc. | 2.0 | g |
| Potassium carbonate sicc. | 75 | g |
| Potassium bromide | 2.0 | g |
| made up with water to 1 litre. | | |

When the individual samples were assessed visually no residual colour of the dye could be observed in the unexposed and developed samples.

To assess the sharpness of the photographic material according to the invention, other samples of it were exposed behind a suitable test image in a conventional densitometer before they were developed in the black-and-white or colour developers described. They were then compared with analogous samples which did not contain any dye to improve the sharpness of the silver iodobromide emulsion.

Before exposure and processing, the emulsion according to the invention has a blue tinge and an absorption maximum of 656 nm. After exposure and processing of the samples according to the invention and of the comparison sample, it could be observed that dye No. 19 according to the invention distinctly improves the sharpness of the photographic material employed.

We claim:

1. A photographic material comprising at least one light-sensitive silver halide emulsion layer and containing at least one photographic layer coloured by a monomethine, trimethine or pentamethine oxonol dye, wherein the improvement dye is at least one monomethine, trimethine or pentamethine oxonol of 1-sulpholanyl-pyrazolone.

2. A light-sensitive material according to claim 1, wherein the dye is a compound of the following formula:

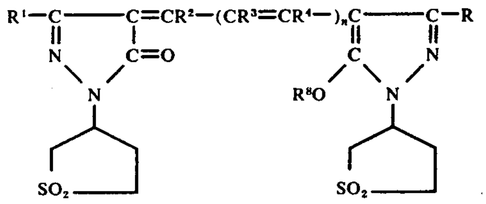

wherein $R^1$ and R denote identical or different alkyl or aryl groups or the groups $COOR^5$ or $CONR^6R^7$;

$R^2$, $R^3$ and $R^4$ are identical or different and denote hydrogen, a lower alkyl group or an aryl group;

$R^5$, $R^6$ and $R^7$ are identical or different and denote hydrogen, alkyl or aryl or $R^6$ and $R^7$ together denote the ring members required to complete a heterocyclic ring;

$R^8$ denotes hydrogen, or a cation capable of forming a watersoluble salt and $n = 0,1$ or 2.

3. A light-sensitive material according to claim 2, wherein $R^1$ and R are identical.

4. A light-sensitive material according to claim 2 wherein $R^2$, $R^3$ and $R^4$ denote hydrogen.

5. A light-sensitive material according to claim 2 wherein $R^1$ and/or R denotes the group $COOR^5$ or the group $CONR^6R^7$ are identical or different and denote hydrogen or a group selected of an alkyl group with from 1 to 18 C-atoms, and a phenyl group which may be substituted, and $R^6$ and $R^7$ may further together denote the ring members required to complete a heterocyclic ring selected of pyrrolidine, piperidine, cyclohexamethyleneimine, indoline, tetrahydroquinoline, morpholine, thiomorpholine, piperazine and n-methyl piperazine rings.

* * * * *